(12) United States Patent
Verhulst

(10) Patent No.: US 8,994,527 B2
(45) Date of Patent: Mar. 31, 2015

(54) SEA FLOOR SAMPLING DEVICE AND METHOD

(76) Inventor: Galen G. Verhulst, Kansas City, MO (US)

( * ) Notice: Subject to any disclaimer, the term of this patent is extended or adjusted under 35 U.S.C. 154(b) by 974 days.

(21) Appl. No.: 12/661,378

(22) Filed: Mar. 16, 2010

(65) Prior Publication Data

US 2010/0238025 A1 Sep. 23, 2010

Related U.S. Application Data

(60) Provisional application No. 61/210,464, filed on Mar. 19, 2009.

(51) Int. Cl.
| | | |
|---|---|---|
| *G08B 1/08* | (2006.01) | |
| *G01N 1/08* | (2006.01) | |
| *E21B 49/02* | (2006.01) | |
| *G01N 33/24* | (2006.01) | |

(52) U.S. Cl.
CPC ............... *G01N 1/08* (2013.01); *E21B 49/025* (2013.01); *G01N 33/241* (2013.01)
USPC .................. 340/539.22; 73/864.63; 116/264; 324/334; 367/17; 367/19; 367/24

(58) Field of Classification Search
CPC ..... G01V 1/3808; G01V 1/3852; G01V 1/38; G01V 1/3817; E02D 1/04; E21B 49/025; G10K 11/006; B63B 22/021
USPC .................. 340/539.22; 73/864.63; 116/264; 324/334; 367/16, 19, 24
See application file for complete search history.

(56) References Cited

U.S. PATENT DOCUMENTS

| | | | | |
|---|---|---|---|---|
| 4,089,209 | A * | 5/1978 | Grana et al. ................. | 73/61.41 |
| 4,196,531 | A * | 4/1980 | Balligand et al. ............... | 37/313 |
| 4,271,704 | A * | 6/1981 | Peters ........................ | 73/864.63 |
| 4,287,763 | A * | 9/1981 | Richard ...................... | 73/863.21 |
| 4,323,988 | A * | 4/1982 | Will et al. ......................... | 367/4 |
| 4,329,883 | A * | 5/1982 | Barnes ....................... | 73/864.52 |
| 4,438,654 | A * | 3/1984 | Torstensson ............... | 73/864.52 |
| 4,962,488 | A * | 10/1990 | Dell-Imagine et al. ........... | 367/3 |
| 5,077,696 | A * | 12/1991 | McEachern et al. ............ | 367/12 |
| 5,444,670 | A * | 8/1995 | Douglas ......................... | 367/90 |
| 6,463,801 | B1 * | 10/2002 | Young et al. ............... | 73/170.32 |
| 6,625,083 | B2 * | 9/2003 | Vandenbroucke .............. | 367/15 |
| 7,965,583 | B2 * | 6/2011 | Thomas ......................... | 367/16 |
| 2002/0110048 | A1 * | 8/2002 | Vandenbroucke .............. | 367/24 |
| 2003/0233894 | A1 * | 12/2003 | Tezuka et al. ................. | 73/865.8 |
| 2004/0231842 | A1 * | 11/2004 | Shammai et al. ............ | 166/264 |
| 2004/0251029 | A1 * | 12/2004 | Horton, III .................... | 166/345 |
| 2005/0219950 | A1 * | 10/2005 | Rowe ............................ | 367/118 |
| 2006/0225810 | A1 * | 10/2006 | Baylot et al. .................... | 141/98 |
| 2007/0106462 | A1 * | 5/2007 | Blain et al. ..................... | 701/207 |
| 2008/0008045 | A1 * | 1/2008 | Basilico ........................ | 367/128 |
| 2009/0084302 | A1 * | 4/2009 | Daran et al. .................. | 114/293 |
| 2009/0095208 | A1 * | 4/2009 | Cardoza et al. ........... | 114/144 B |
| 2009/0149092 | A1 * | 6/2009 | Jaber et al. ...................... | 441/22 |
| 2009/0195251 | A1 * | 8/2009 | Darnet et al. ................ | 324/334 |
| 2009/0218136 | A1 * | 9/2009 | Asakawa et al. ................. | 175/6 |
| 2009/0257312 | A1 * | 10/2009 | Novick et al. ................. | 367/119 |
| 2009/0262600 | A1 * | 10/2009 | Railey et al. ...................... | 367/5 |
| 2009/0272203 | A1 * | 11/2009 | Johnson et al. ............ | 73/864.43 |
| 2009/0287414 | A1 * | 11/2009 | Vickery ...................... | 701/220 |

(Continued)

*Primary Examiner* — Benjamin Lee
*Assistant Examiner* — Quang D Pham

(57) ABSTRACT

A device for collecting samples of the sea floor, including a collection apparatus, a diving apparatus and a control apparatus.

10 Claims, 8 Drawing Sheets

(56) References Cited

U.S. PATENT DOCUMENTS

2009/0294129 A1* 12/2009 Judge et al. .................. 166/341
2010/0001735 A1* 1/2010 Combee ....................... 324/344
2012/0087208 A1* 4/2012 Thompson et al. ............ 367/20
2014/0377873 A1* 12/2014 Hay .............................. 436/29

* cited by examiner

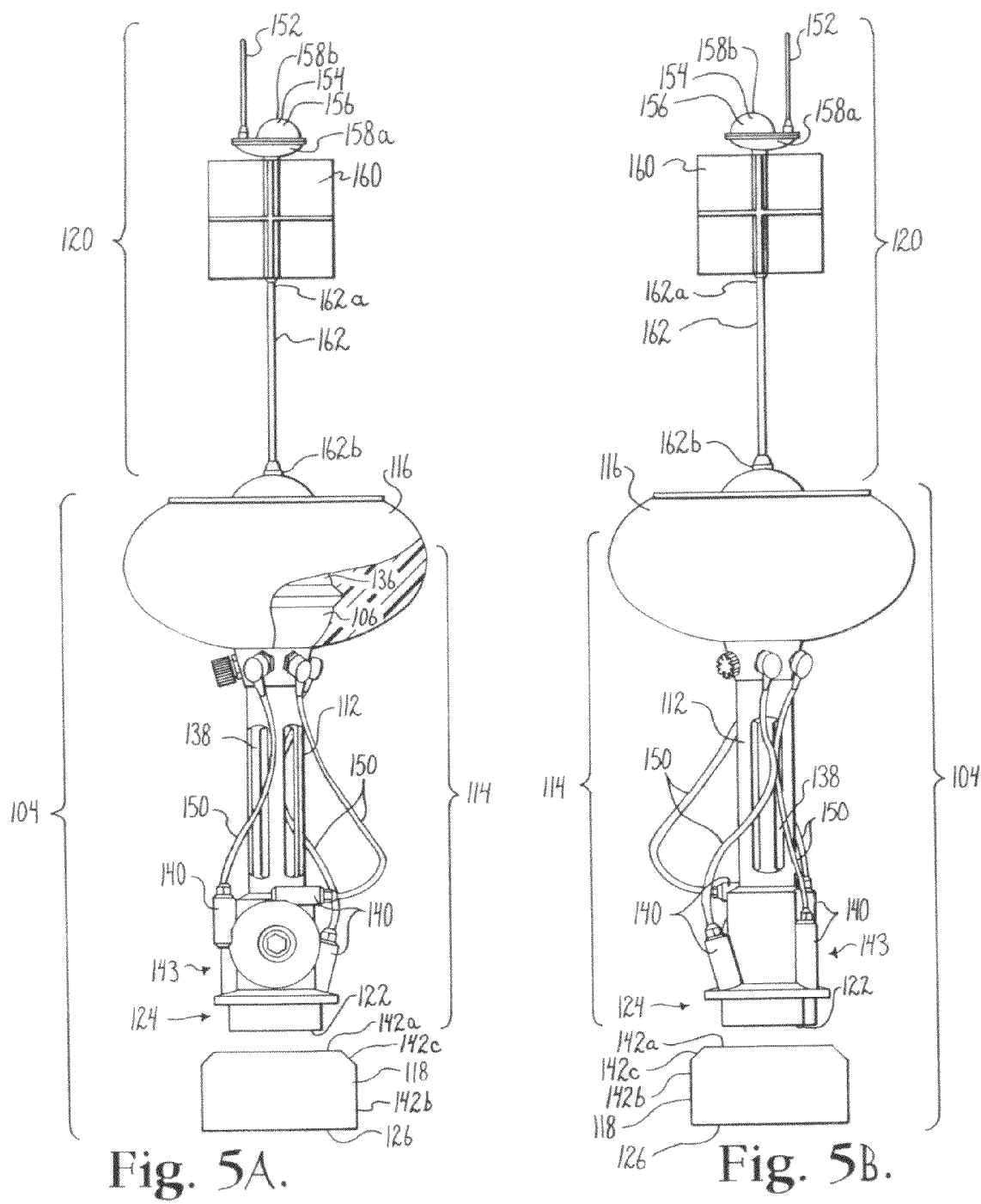

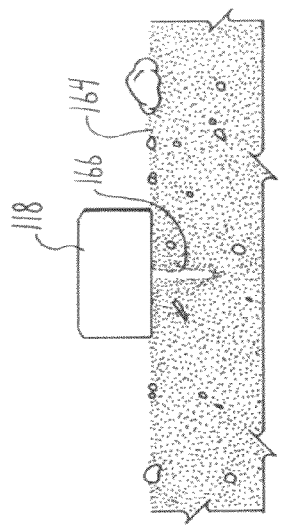
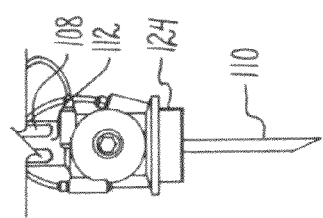
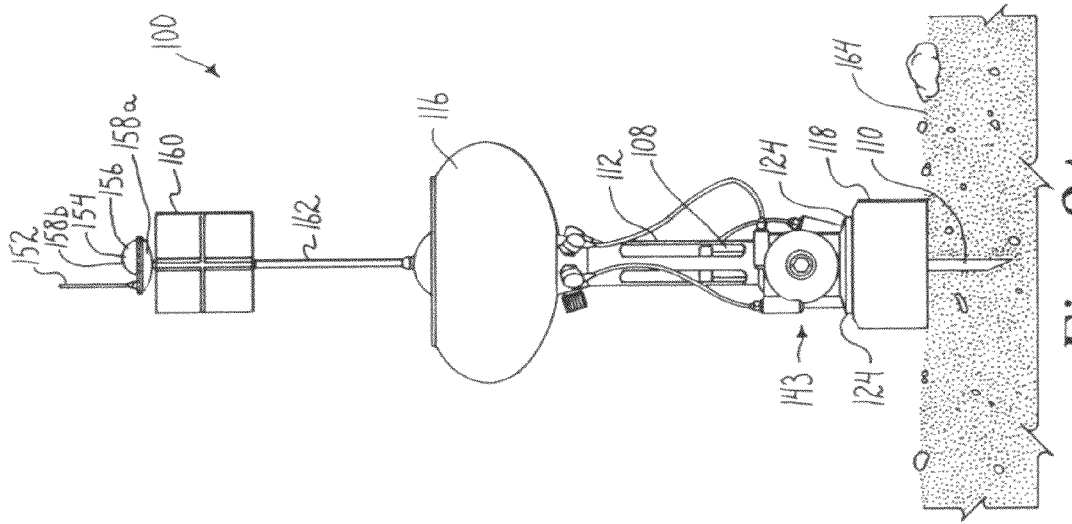
Fig. 9B.
Fig. 9A.

SEA FLOOR SAMPLING DEVICE AND METHOD

CROSS-REFERENCE TO RELATED APPLICATIONS

This application claims the benefit of U.S. Provisional Patent Application Ser. No. 61/210,464, filed Mar. 19, 2009 and incorporated by reference herein.

BACKGROUND OF THE INVENTION

It has been estimated that at least 1.3 trillion barrels of oil and gas exist below the sea floor. Deep water drilling occurs at depths generally greater than 1,000 feet. For example, in Brazil's ultra-deep oil fields, producers have to go through 7,000 feet of water, over 10,000 feet of sand and rocks as well as another 6,000 feet of salt, to extract the oil. This presents a variety of technical challenges. In addition, reaching the oil and gas is dangerous and expensive. For example, in 2007, the day rate alone for renting a drilling rig was over $500,000. Offshore oil exploration traditionally involves the repeated firing of large underwater air guns, fired from a ship, to create seismic pulses. These pulses are used for sonar-like mapping of rock layers beneath the seabed. The cost of operating such a ship is extremely high. Additionally, it is believed that these practices cause substantial harm to marine mammals, especially whales.

SUMMARY OF THE INVENTION

A deep sea floor sampling device that has a sampling apparatus, a diving apparatus and a control apparatus. The sampling apparatus includes a sample ampule with first and second ends and an interior chamber (e.g., an ampule chamber or interior), a sampling spike with a tip for penetrating the sea floor and a barrel opening onto the tip and connected to the first end of the sample ampule through an actuation valve located between the sampling spike and the sample ampule, the valve having an open position wherein the chamber of the sample ampule is in fluid flow communication with the barrel of the sampling spike and a closed position wherein fluid flow is blocked between the barrel and the ampule chamber. The diving apparatus includes a balance weight operably joined to the sampling apparatus by a selectively activatable release and a float, wherein the balance weight is releasably attached to the sample apparatus. The float is attached to the second end of the sample ampule, whereby the device is maintained in a substantially vertical orientation; the weight being sized relative to the sampling apparatus such that the overall density of the apparatus is greater than water, when the weight is attached, so that the apparatus sinks when the weight is attached to the apparatus and the float being sized relative to the sampling apparatus such that, when the weight is released from the apparatus, the density of the apparatus is less than water and the apparatus rises in water. The control apparatus includes system electronics, having a sensor system to operably sense when the apparatus is on the sea floor, to open and close the activation valve and to release the weight after the valve is closed and a communication subassembly having at an antenna for signaling for pick up on a water surface.

In a further embodiment, the balance weight includes a weight substantially sufficient to sink the device from the sea surface to the sea floor.

In a further embodiment, the balance weight has a metal sinker configured and arranged to sink the device to a depth of at least about 5,000 feet.

In a further embodiment, the float has an amount of air sufficient to raise the device from the sea floor to the sea surface.

In a further embodiment, the balance weight includes a bottom end and the sample needle extends at least about 12-inches past the bottom end of the balance weight.

In a further embodiment, the sample ampule is pressurized.

In a further embodiment, the communication subassembly includes at least one of an RF antenna, a G.P.S. antenna and a light.

In a further embodiment, the communications assembly includes a radar angle reflector.

In a further embodiment, the at least one sensor is selected from the group consisting of a drift sensor, a depth sensor, a pressure sensor, and a temperature sensor.

In a still further embodiment, a method of collecting a sample of the deep sea floor includes the steps of sinking from the water surface to the sea floor; penetrating the sea floor with a tip of a spike; embedding the spike into the sea floor; collecting a sample of the sea floor in a barrel of the spike; transferring the collected sample from the barrel of the spike into a sample ampule; returning to the water surface; and emitting a signal.

In a further embodiment, continuously detecting the drift of the device.

In a further embodiment, adjusting the density of the apparatus at the water surface to be greater than that of the water and after collecting the sample modifying the density of the apparatus to be less than the density of the water.

In a further embodiment, modifying the density of the apparatus relative to the water after collecting the sample includes releasing a balance weight.

In a further embodiment, collecting at least one of depth information, drift information, temperature information and pressure information.

In a further embodiment, activating an actuation valve between the sample spike and the sample ampule, whereby the barrel of the spike is in fluid flow communication with the sample ampule.

In a further embodiment, actuating the actuation valve includes moving the actuation valve from a first position to a second position.

In a further embodiment, emitting a signal includes emitting at least one of an RF signal, a G.P.S. signal and light.

The present invention is a wireless and self-contained device that provides rapid and low cost collection of water and core samples from the deep sea floor, at depth, which can be analyzed for oil and gas. On-board sensors provide improved data collection for accurately locating under water pockets of oil and gas. Manufacture and exploration costs are reduced due to the simplicity and relatively small size of the device, relative to traditional detection methods and devices, such as remote-control deep water submarines and the like.

Other advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 5A is a front view of the sampling device of FIG. 1 especially showing a diving apparatus thereof.

FIG. 5B is a rear view of the diving apparatus of FIG. 5A.

FIG. 9A is a schematic side elevational view illustrating the sampling device of FIG. 1 on the sea floor.

FIG. 9B is a schematic side elevational view illustrating a portion of the sampling device of FIG. 9B, after release of the balance weight.

DETAILED DESCRIPTION OF THE ILLUSTRATED EMBODIMENT OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figures 1, 2:
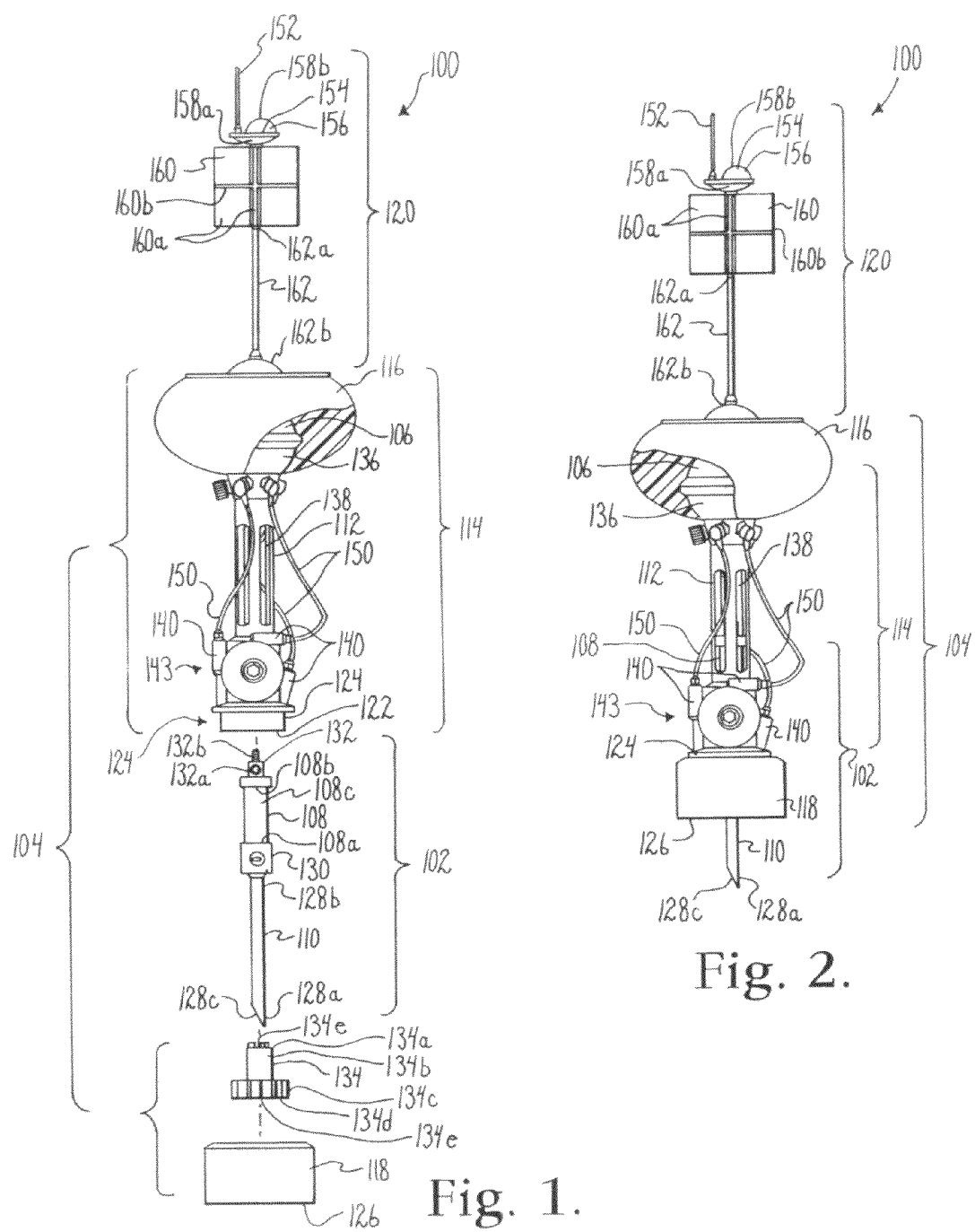
FIG. 1 is a partially assembled, cut away front view of a deep sea sampling device in accordance with one embodiment of the present invention, with portions removed to show detail thereof.
FIG. 2 is a front view of a fully assembled deep sea sampling device of FIG. 1, with portions removed to show detail thereof.
Figure 3:
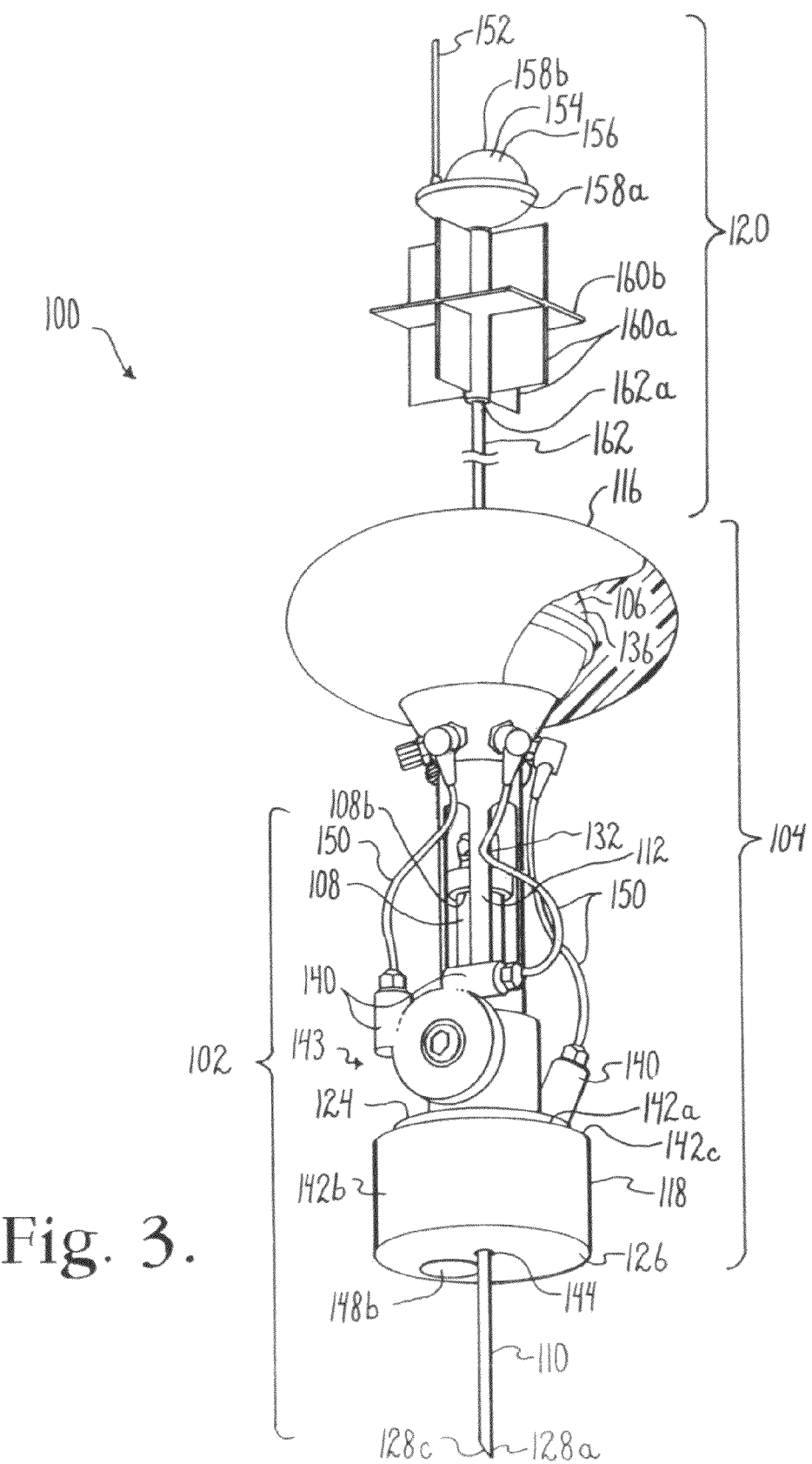
FIG. 3 is a perspective view of the deep sea sampling device of FIG. 2, with portions removed to show detail thereof.

FIGS. 1-3 illustrate a deep sea floor sampling device generally indicated by the reference numeral 100. The deep sea floor sampling device 100 includes three major components, a sampling apparatus 102, a diving apparatus 104, and a control apparatus 106.

The sampling apparatus 102 includes a sample ampule 108 with first and second ends 108a, 108b and an interior chamber 108c, and a sampling spike 110 attached thereto. The sampling apparatus 102 is received into an ampule housing 112 of a diving subassembly 114 of the diving apparatus 104, such that the sampling apparatus 102 is maintained in a generally vertical orientation.

The diving apparatus 104 includes the diving subassembly 114, which can include at least a portion of the control apparatus 106, such as at least some of the system electronics, a float 116 and a releasably attached balance weight 118. A communication subassembly 120 is attached to the top of the device via the float 116 (e.g., the top of the float 116).

FIG. 1 illustrates the deep sea floor sampling device 100 prior to full or final assembly (e.g., prior to preparation for a dive). The sampling apparatus 102 is aligned with the bottom end 122 of the diving apparatus 104, such that the sampling apparatus 102 can be inserted into the ampule housing 112. The ampule housing 112 is configured and arranged to receive the ampule 108, and optionally the actuation valve 130, of the sampling apparatus 102. After the sampling apparatus 102 has been inserted into (e.g., releasably engaged by) the diving apparatus 104, the balance weight 118 is attached to (e.g., releasably engaged by) the bottom end 122 of the diving apparatus 104, such as via an attachment subassembly 124.

FIGS. 2-3 illustrate the deep sea floor sampling device 100 after assembly. The sample ampule 108 of the sample apparatus 102 is housed in the ampule housing 112 (e.g., received therein and stabilized and protected thereby). The balance weight 118 is attached to the bottom end 122 of the diving apparatus 104, and the spike 110 of the sample apparatus 102 extends through the balance weight 118, such that the spike 110 extends a distance past the bottom surface 126 of the balance weight 118.

FIGS. 4A-4D illustrate a sampling apparatus 102, which includes a sample ampule 108 having a sample spike 110 attached thereto. The sample ampule 108 includes first and second ends 108a, 108b, and an interior chamber 108c configured and arranged for receipt of a sample. The sample ampule 108 can be formed of glass, metal, plastic or ceramic. In some embodiments, the sample ampule 108 is sized to receive and contain a sample (e.g., a core sample of the sea floor and/or water) having a length of between about 0.01, 0.05, 0.1, 0.2, 0.3, 0.4, or 0.5-mm and about 0.6, 0.7, 0.8, 0.9, 1.0, 1.1, 1.2, 1.3, 1.4, or 1.5-mm or more, and a diameter of between about 5, 10, 15, 20, 25, 30, 35, 40, 45, or 50-mm and about 55, 60, 65, 70, 75, 80, 85, 90, 95, or 100-mm or more in diameter. In other embodiments, the sample ampule 108 is sized to receive and contain a larger sample having a length of between about 0.1, 0.2, 0.3, 0.3, 0.4, 0.5, 0.6, 0.7, 0.8, 0.9, or 1.0-meters and about 1.25, 1.5, 1.75, 2.0, 2.25, 2.5, 2.75, 3.0, 3.25, 3.5, 3.75, or 4.0-meters or more, and a diameter of between about 5, 10, 15, 20, 25, 30, 35, 40, 45, and 50-mm and about 55, 60, 65, 70, 75, 80, 85, 90, 95, and 100-mm or more in diameter. Accordingly, the ampule housings 112 is configured and arranged to receive a specifically sized ampule 108, such that there is a snug fit there between. For example, in one embodiment, the ampule housing 112 is configured and arranged to receive a smaller ampule 108, while in another embodiment, the ampule housing 112 is configured and arranged to receive a larger ampule 108.

The ampule 108 is pressurized using methods known in the art, such that atmospheric pressure is maintained within the ampule 108 (e.g., within the interior chamber 108c) as the sampling device 100 descends to the sea floor. For example, the sample ampule 108 is configured and arranged to maintain a pressurized seal at a working depth of from at least about 1,000, 1,500, 2,000, or 2,500-meters to about 3,000, 3,500, 4,000, 4,500 or 5,000-meters or more. The pressure can be released when the device 100 is below the water's surface (e.g., descending to the sea floor and/or at the sea floor), such as by opening a valve, such that a sample (e.g., a core sample) can enter the interior 108c of the ampule 108, as described below.

The spike 110 is a generally rigid tube having a tip 128a for penetrating the sea floor, a connection end 128b and a hollow barrel 128c opening onto the tip 128a. The barrel 128c extends from the connection end 128b to the tip 128a. The spike 110 is connected to the first end 108a of the sample ampule 108 through an actuation valve 130 that is located between the connection end 128b of the sampling spike 110 and the sample ampule 108. While the tip 128a is illustrated as being pointed, in some embodiment, the tip 128a is blunt or rounded. The actuation valve 130 can be any pressure valve known in the art, such as but not limited to a ball valve. The actuation valve 130 includes open and closed positions and can be controlled by the control apparatus 106 (e.g., system electronics). When the actuation valve 130 is in the open position, the interior 128c of the ampule 108 is in fluid flow communication with the barrel 128c of the spike 110. When the actuation valve 130 is in the closed position wherein fluid flow is blocked between the barrel 128c and the ampule chamber 128c. When the device 100 descends to the sea floor, the spike 110 penetrates the sea floor. A portion of the sea floor (e.g., a core sample) and/or water enters and optionally fills the barrel 128c. In some embodiments, the spike 110 includes one or more small or minute holes at or near its connection end 128c, such that water within the barrel 128c can be evacuated from the barrel 128c as the barrel 128c is filled with the sample.

At the second end 108c of the ampule 108, the sampling apparatus 102 includes a gas valve 132, through which gas can be delivered to the ampule chamber 108c. In some circumstances, some of the contents within the ampule chamber 108c can be removed through the gas valve 132. The gas valve 132 includes an actuation nut 132a, for operating (e.g., opening, closing) the gas valve 132, and a tubing connector 132b, for connecting the gas valve 132 to tubing, such as but not limited to gas tubing. In some embodiments, the gas valve 132 is configured and arranged such that a sample within the ampule chamber 108c can be removed through the tubing connector 132b.

Figure 4A:
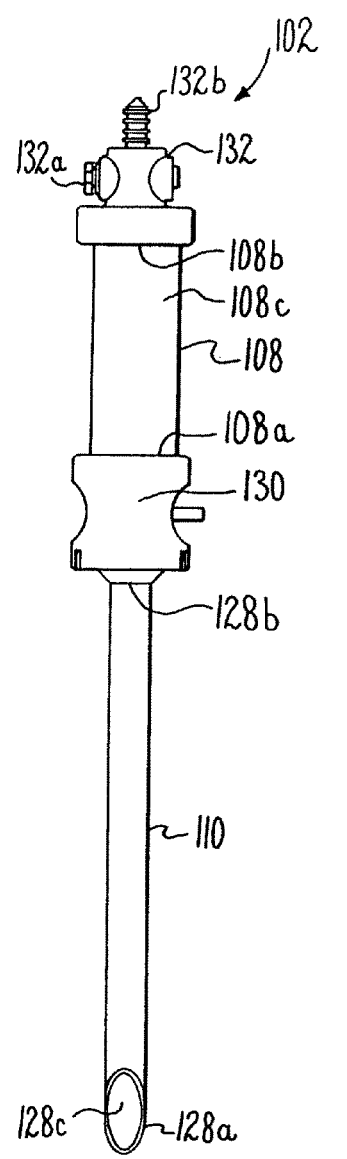
FIG. 4A is a front view of a collection apparatus of the sampling device of FIG. 1, in one embodiment.
Figure 4B:
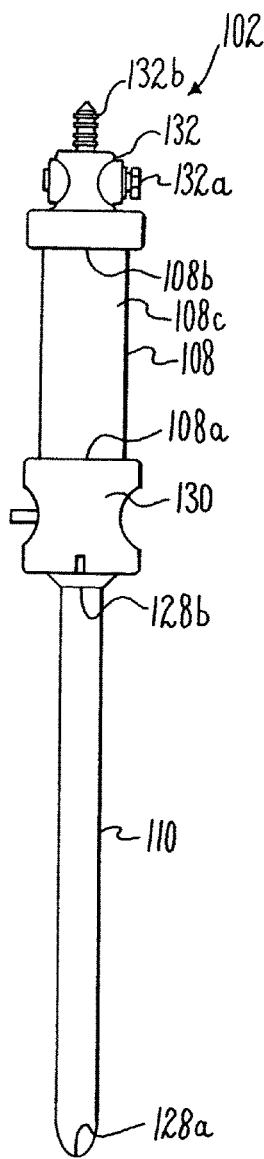
FIG. 4B is a rear view of the collection apparatus of the sampling device of FIG. 4A.
Figure 4C:
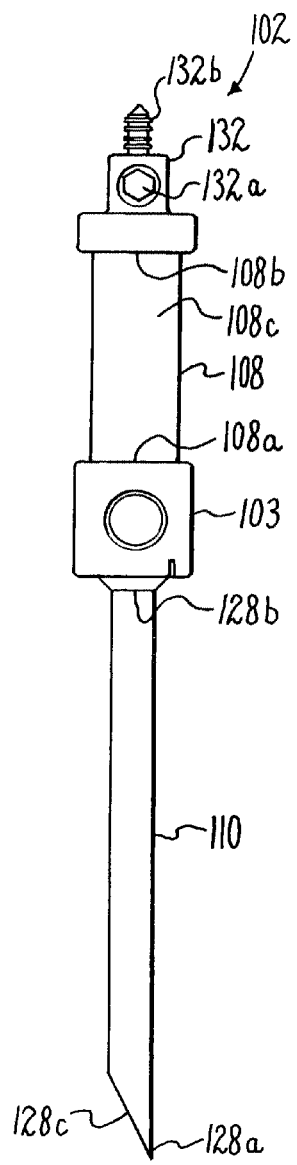
FIG. 4C is a first side view of the collection apparatus of the sampling device of FIG. 4A.
Figure 4D:
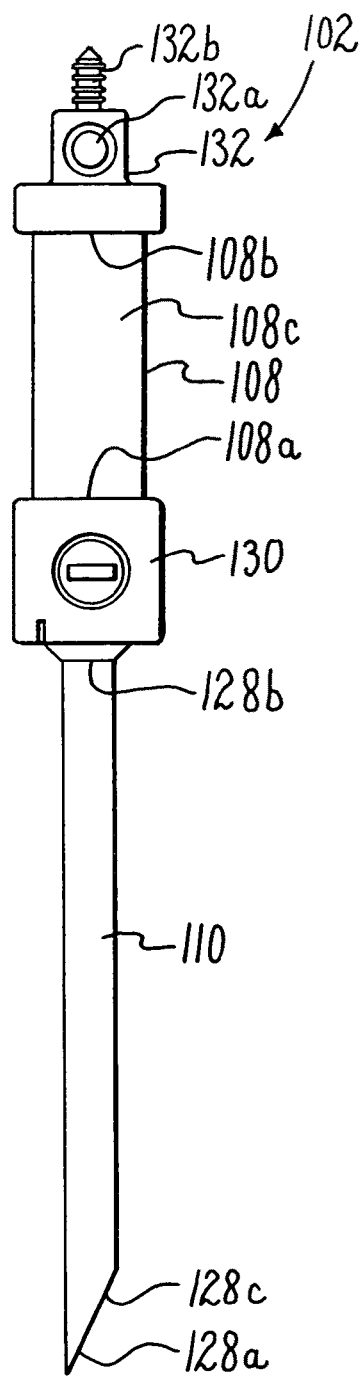
FIG. 4D is second side view of the collection apparatus of the sampling device of FIG. 4A.
Figure 4F:
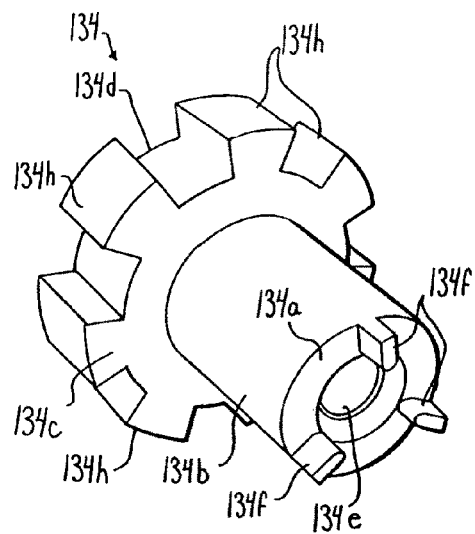
FIG. 4F is a perspective view of a spike guide of the sampling device of FIG. 1.
Figure 4E:
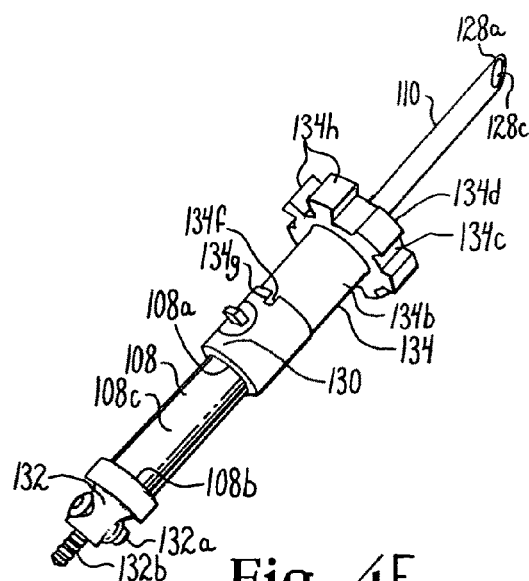
FIG. 4E is a perspective view of the collection apparatus of the sampling device of FIG. 4A, with a spike guide included.

Referring now to FIGS. 4E-4F, a spike guide 134 is removably mounted on (e.g., slides over) the spike 110 of the sampling apparatus 102. The spike guide 134 includes a first end 134a, a barrel portion 134b, a spacing portion 134c and a second end 134d. A spike channel 134e extends through the spike guide 134, from the first end 134a to the second end 134d. The spike channel 134e is configured and arranged (e.g., sized) to receive the spike 110 therethrough, such that a portion of the spike 110 extends out of the spike channel 134e and past the second end 134d. In some embodiments, the spike 110 extends a sufficient distance past the second end 134d of the spike guide 134, that when the balance weight 118 is attached, the spike 110 extends at least 12-inches past the bottom 126 of the balance weight 118. In some embodiments, the first end 134a of the spike guide 134 includes one or more detents 134f configured and arranged to releasably interlock with a detent cup 134g on the bottom end of the actuation valve 130. The spike guide 134 slides over the spike 110, such that the detent(s) 134f engage the detent cup(s) 134g, such that the spike guide 134 is substantially prevented from twisting about the spike 110. The spacing portion 134c of the spike guide 134 can include one or more extensions 134h, configured and arranged to maintain a linear axis of the spike 110 (e.g., the linear axis of the spike extends from the spike's tip to the spike's connection end) in a substantially parallel orientation with respect to a linear axis of the diving apparatus 104. This ensures that the spike 110 is substantially vertical when it penetrates the sea floor. The bottom end 134d of the spike guide 134 is configured and arrange to releasably engage the balance weight 118, such as is described in greater detail below.

Referring now to FIGS. 1-3, 5A, 5B, 6, and 7A-7D, the diving apparatus 104 includes a diving subassembly 114, a balance weight 118 and a float 116. The float 116 is attached to the diving subassembly 114, such as covering the control apparatus 106 (e.g., a housing 136 for at least some of the system electronics). In some circumstances, a water-tight seal (e.g., a pressurized seal) is formed between the float 116 and the diving subassembly 114. A communication subassembly 120 is attached to the diving apparatus 104, such as by attachment to the float 116 (e.g., the top, see FIGS. 5A-5B).

In some embodiments, the float 116 is formed of foam (e.g., closed-cell foam). In other embodiments, the float 116 is a hollow chamber containing a gas, such as air or helium. In preferred embodiments, the float 116 is sized such that the density of the device 100 without the balance weight 118 (e.g., after release of the balance weight) is less than the density of the surrounding water. Accordingly, when the balance weight 118 is not attached, the device 100 substantially floats. Thus, when the device 100 is at the sea floor and the balance weight 118 is released, the device 100 can ascend to the water's surface.

The diving subassembly 114 (e.g., see FIG. 6) includes the ampule housing 112, a control housing 136 for at least a portion of the system electronics (e.g., at least a portion of the control apparatus 106), and an attachment subassembly 124. The ampule housing 112 is configured and arranged to receive (e.g., releasably mate with, releasably engage) at least the ampule 108 of the sampling apparatus 102. In some embodiments, bot the ampule 108 and the actuation valve 130 are configured and arranged to substantially fit within the ampule housing 112. The ampule housing 112 is formed of an impact-resistant material that can protect an ampule 108 within, such as but not limited to steel and plastic. Use of a lighter density, impact-resistant plastic is preferred over steel, in some circumstances, for reducing the density of the overall device 100 and thus reducing the size requirements of the float 116 and the balance weight 118. The ampule housing 112 is a tube having an interior of sufficient diameter to receive the ampule 108. One or more windows 138 can be included in the ampule housing 112, such that at least a portion of the ampule 108 can be viewed after loading into the ampule housing 112. Alternatively, the ampule housing 112 is a steel wire or mesh cage.

The control housing 136 is a sealed and/or pressurized plastic or metal vessel (e.g., container), such that water cannot penetrate therethrough during device 100 operation (e.g., diving to the sea floor and returning to the water's surface). While the control housing 136 is illustrated as spherical, it can have any other three-dimensional shape, such as but not limited to cuboidal or pyramidal. At least a portion of the system electronics (described elsewhere herein) are contained within the control housing 136. A battery (e.g., a lithium ion battery) is also housed within the control housing 136. Electronics within the control housing 136 can be connected to other electronic components (e.g., control components) via wires housed within tubing, such as is known in the art. In some embodiments, the control housing 136 includes one or more exterior controls for accessing the systems electronics housed within, for opening the control housing 136, and the like. The bottom end of the float 116 is configured and arranged to receive (e.g., attached to) the control housing.

An attachment subassembly 124 is located at the bottom end 122 of the diving subassembly 114, and is configured and arranged to releasably attach the balance weight 118 to the bottom end of the device 100. The attachment subassembly 124 includes one or more attachment devices known in the art, such as but not limited to hooks, pins and locks. The attachment subassembly 124 includes a drive gear subassembly 143, which includes at least one actuator 140, for releasing the balance weight 118 from the attachment subassembly 124. For example, in one embodiment, a plurality of actuators 140 are configured and arranged to open a plurality of locking pins attaching the balance weight 118 to the diving subassembly 114, whereby the balance weight 118 is released. The drive gear subassembly 143 and actuators 140 can include electronics, a solenoid, a gas valve, and the like.

As shown in FIGS. 7A-7D, the balance weight 118 includes a top 142a, a side 142b, and a bottom 126. In some embodiments, the balance weight includes a shoulder 142c. The balance weight 118 has a spike channel 144 and is releasably attached to the sample apparatus 102 such that the spike 110 extends downwardly through the spike channel 144. In some embodiments, the spike 110 extends at least about 5, 6, 7, 8, 9, 10, 11, 12, 13, 14, or 15-inches past the bottom 126 of the balance weight 118. A spike guide receptacle 146 is located in the top 142a of the balance weight 118, and is configured and arranged to releasably engage the spacing portion 134c of the spike guide 134 (e.g., when the spike guide 134 is releasably engaged with the spike 110). For example, the floor 146a of spike guide receptacle 146 contacts the second end 134d of the spike guide 134, and the extensions 134h of the spacing portion 134c contact the wall 146b of the spike guide receptacle 146. In a further example, the spike channel 144 extends from the floor 146a of spike guide receptacle 146 to the bottom 126 of the balance weight 118. One skilled in the art understands that when the float 116 is attached to the diving subassembly 114 (e.g., the second end of the sample ampule 108) and the balance weight 118 is attached to the attachment subassembly 124, the device 110 is maintained in a substantially vertical orientation.

Referring again to FIGS. 7A-7D, the balance weight 118 includes a depth finder channel 148 that extends from the top 142a to the bottom 126 of the balance weight 118. In preferred embodiments, the wall 148a of the depth finder channel 148 slants generally outwardly, from the top of the balance weight to the bottom of the balance weight. Accordingly, the lower orifice 148b has a greater diameter than that of the upper orifice 148c. This ensures that the signal of a depth finder (e.g., a depth sensor), such as but not limited to a sonic (e.g., sonar) depth finder, does not substantially contact the wall 148a of the depth finder channel 148.

The balance weight 118 is sized relative to the sampling apparatus 102 such that the overall density of the apparatus (e.g., the device 100) is greater than water so that the apparatus sinks when the balance weight 118 is attached to the apparatus 100, and the float 116 is sized relative to the sampling apparatus 100 such that when the weight 118 is released from the apparatus 100, the density of the apparatus 100 is less than water and the apparatus 100 rises when in water. For example, the weight of the balance weight 118 is substantially sufficient to sink the device 100 from the sea surface to the sea floor. In a further embodiment, the balance weight 118 is a metal sinker configured and arranged to sink the device 100 to a depth of at least about 1,000, 2,000, 3,000, 4,000, or 5,000-feet or more. In another example, the float 116 has a buoyancy (e.g., density) sufficient to raise the device 100 from the sea floor to the sea surface, when the balance weight 118 has been released from the bottom end (e.g., attachment subassembly 124) of the diving apparatus 104.

The control apparatus 106 includes the system electronics (including a sensor system) configured and arranged to operably sense (e.g., detect) when the apparatus 100 is on the sea floor, to open and close the actuation valve 130 (e.g., activation valve) and to release the balance weight 118 after the valve 130 is closed. In some embodiment, the control apparatus 106 includes at least some of the communication subassembly 120. The communication subassembly 120 has an antenna, such as described below, for signaling for pick up on a water surface. In some embodiments, the control apparatus 106 includes at least some of the connection subassembly 124, such as electronics associated with the connection subassembly 124 and for operation thereof.

Depending upon configuration of the device 100, some or all of the system electronics (e.g., the control apparatus 106) can be contained within the control housing 136. One or more portions of the system electronics can be located elsewhere in the device 100. For example, at least a portion of the system electronics can be associated with (e.g., physically via a wired connection, or wirelessly) the attachment subassembly 124. For example, the actuators 140 can include local circuitry (e.g., located with the actuator 140 and controls operation of a solenoid) which is connected via wires 150 to system electronics located in the control housing 136. In another example, a portion of the system electronics can be physically associated with the sampling apparatus 102. In another example, a portion of the electronics located on the sampling apparatus 102 can interact (e.g., via a plug and socket connection or wirelessly) with another portion of the electronics located within the ampule housing 112. For example, when the ampule 108 is received by the ampule housing 112, an electronic connection is made between electronics included in the ampule 108 and electronics included in the ampule housing 112.

The system electronics include electronic components (e.g., circuitry, processor or microprocessor), memory, programming, sensors, transceivers, battery, solenoids, such as is known in the art, for operating the device 100. For example, the system electronics include electronic components and programming for actuating the actuation valve 130 of the sampling apparatus 102. In another example, the system electronics include electronic components and programming for opening the actuation valve 130, to transfer a sample in the barrel 128c of the spike 110 into the chamber 108c of the ampule 108. Programming can include instruction for descending and ascension procedures, sample collection procedures, data handling procedures, release of the balance weight, remote communication with a ship, and the like.

The system electronics (e.g., included in the control apparatus 106) include at least one sensor, for detecting properties of the area surrounding the device 100. For example, the device 100 includes a drift sensor, which includes a gyroscope, for detecting drift of the device 100 (e.g., lateral drift, angle of descent, angel of ascent) as it sinks to the sea floor and as it rises to the water's surface. Inclusion of a drift sensor enables more accurate determination of the sample collection site (after the device is retrieved), in spite of device drifting due to ocean currents.

In another example, the system electronics include a depth finder, such as but not limited to a sonar (e.g., sonic depth finder). In some circumstances, the depth finder is located in the bottom end 122 of the diving apparatus 114, is aligned with the depth finder channel 148 of the balance weight 118, and is pointed in a generally downward direction, such that signals produced by the depth finder do not interact with the channel wall 148a. The depth finder can be configured to detect the bottom of the sea floor and/or the actual depth of the device (e.g., at a time point). For example, the depth finder can be configured and arranged to detect the sea floor (e.g., bottom surface location) when the device 100 is within less than 200, 175, 150, 125, 100, 75, 50, 40, 30, 20, or 10-meters or less of the sea floor. Advantageously, the device 100 can determine how close it is to the bottom of the sea floor as it descends and rises (e.g., ascends), and can determine the depth (of the sea floor) at which a core sample is/was taken.

In another example, the system electronics include a pressure sensor, for detecting the water pressure (e.g., changes therein) as the device 100 descends and rises. For example, the pressure sensor can be configured to initiate ascension procedures when the device 100 exceeds about 4,200-meters in depth. In still another example, the system electronics include a temperature sensor, for detecting the water temperature around the device 100. Additional sensors known in the art, such as moisture sensors, can be included in the device 100.

Figure 8:
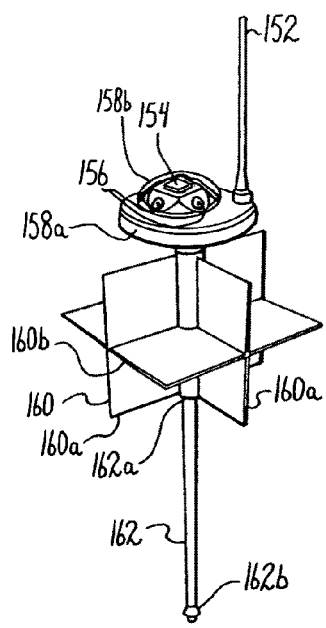
FIG. 8 is a perspective view of a communication subassembly of the sampling device of FIG. 1.
Figure 6:
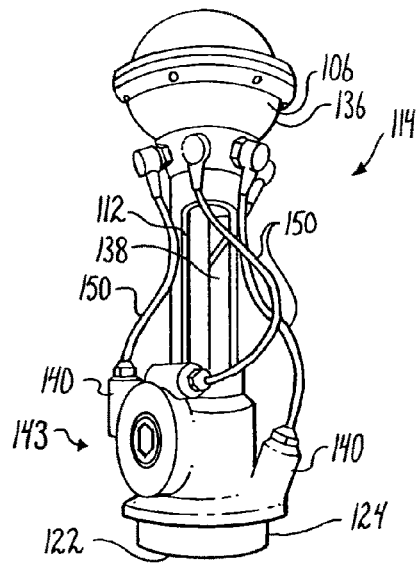
FIG. 6 is a perspective view of a diving subassembly with portions removed to show detail thereof.
Figure 7A:
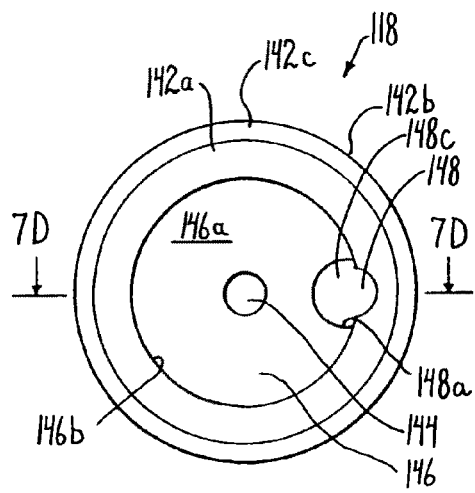
FIG. 7A is a top view of a balance weight.
Figure 7B:
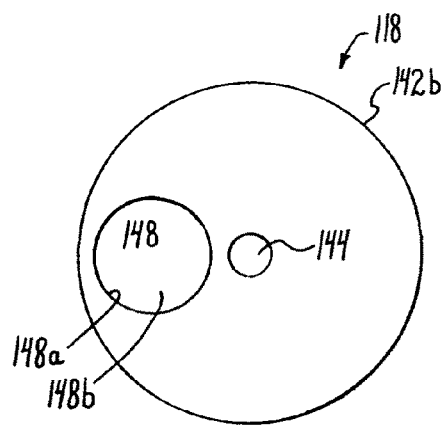
FIG. 7B is a bottom view of the balance weight of FIG. 7A.
Figure 7D:
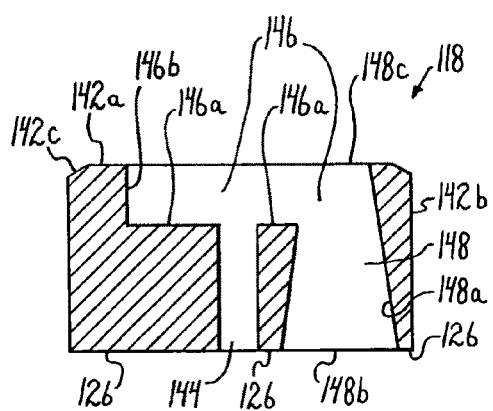
FIG. 7D is a cross-sectional view of the balance weight of FIG. 7A, taken on line 7D-7D.
Figure 7C:
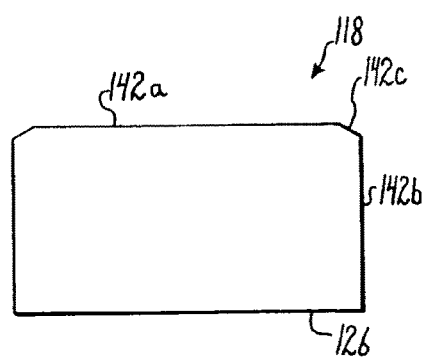
FIG. 7C is a side view of the balance weight of FIG. 7A.

Referring now to FIG. 8, as described elsewhere herein, the device 100 includes a communications subassembly 120. In the illustrated embodiment, the communications subassembly 120 is attached to the top of the diving apparatus 104 (e.g., at the top of the float 116), such as shown in FIGS. 1-2. However, in other embodiments, all or part of the communications subassembly 120 is located elsewhere within the device 100. For example, an antenna can be located within the float 116 or within the control housing 136 of the control apparatus 106. In the illustrated embodiment, the communication subassembly includes an RF antenna 152 (e.g., radio transceiver), a G.P.S. locator 154 (e.g., G.P.S. antenna), and at least one light 156, which are housed within a communications housing 158. The communications housing 158 includes a base 158a, from which the RF antenna 152 extends in a generally vertical orientation, and a cover 158b. The cover 158b is generally clear and colorless plastic, such that the lights 156 can be seen therethrough. The lights 156 are configured and arranged to project in each of four (4) directions within a plane, wherein the directions are separated by 90° angles. The radio transceiver 152 has a range of at least about 20-miles and a mapping locator, for ship radar tracking up to about 10-miles. The communications subassembly further includes a radar angle deflector 160 (e.g., radar deflector) located below the communications housing 158. The radar deflector 160 is preferably formed of metal and includes at least one vertical fin 160a and at least one horizontal fin 160b (e.g., see FIG. 8). The device 100 can be detected by radar signals from a remotely located ship impinging upon the radar deflector 160, and then bouncing back to the ship, such as is known in the art. The communication subassembly 120 includes a mast 162 for lifting the antennae 152, 154, lights 156 and radar deflector 160 above the surface of the water (e.g., about 1, 2, 3, 4-feet or more above the water's surface), thereby improving device 100 detection via a searching vessel (e.g., ship).

FIGS. 9A and 9B illustrate a method of collecting a sample of the sea floor 164, in one embodiment. The device 100 of the illustrated embodiment is put into the ocean and sinks (e.g., descends) from the water's surface to the sea floor 164. As shown in FIG. 9A, when the device 100 reaches the sea floor 164, the bottom of the balance weight 110 rests on (e.g., contacts) the surface of the sea floor 164. The spike 110 penetrates the surface of the sea floor 164 and is embedded in the sea floor 164, thereby receiving (e.g., collecting) a sample (e.g., a core sample) of the sea floor 164 into the barrel 128c of the spike 110. The sample is transferred (e.g., from the barrel 128c of the spike 110) into the ampule 108 (e.g., according to (e.g., in response to) instruction by the system electronics (e.g., programming of the control system 106). Then, as illustrated in FIG. 9B, the device 110 releases the balance weight 118 (e.g., according to (e.g., in response to) instruction by the system electronics (e.g., programming of the control system 106)) and floats (e.g., ascends) to the water's surface. When the spike 110 is removed from the sea floor 164, a hollow space 166 (corresponding in size to the size of the sample) is left in the ocean floor 164. At the water's surface, the device 100 sends radio, G.P.S., and/or light signals (e.g., in response to system electronics instructions (e.g., programming)), and is retrieved by a ship. The ampule 108 (e.g., containing the sample) can be removed from the device 100, for storage, testing and/or the like. Additionally, data associated with the collected sample (e.g., drift information, depth information, temperature and pressure information and the like) can be retrieved from the system electronics (e.g., transferred, downloaded, saved), for use in determining the location where the sample was collected, water conditions, and the like.

A variety of data (e.g., information) related to collection of the sample is collected and stored by the device 100. For example, the drift of the device 100 is detected (e.g., drift information is collected, such as via sensors and the system electronics (e.g., the control apparatus 106)), such as when the device 100 is descending to and/or ascending from the sea floor 164. For example, a drift sensor, including a gyroscope, detects lateral motion (e.g., angle of descent) of the device 100. It is known that ocean currents can push a device 100 away from the location where it was put into the water. Accordingly, tracking drift of the device 100 away from the drop location enables accurate determination of the location of core sample collection relative to the drop location.

In another example, depth information is collected (e.g., via sonar detector(s) and system electronics) at least while the device 100 is descending to the sea floor 164. For example, a sonar detector located in the attachment assembly 124 and directed generally downward (e.g., through sonar depth finder channel 148 of the balance weight 118) sends sonar signals that are detected and used to determine the location (e.g., proximity) of the sea floor 164, and optionally to track the approach of the sea floor 164 as the device 100 descends thereto. Depth information enables personnel (e.g., a user) to determine the depth at which a sample was collected, and thus to estimate how far they must drill to reach oil and/or gas associated with the collected sample. In addition to drift and depth information, temperature information and pressure information can be detected. System electronics are configured and arranged to receive and record (e.g., hold, remember) the collected information, such as for use by personnel after the device 100 is retrieved.

Referring again to FIG. 9A, when the device 100 reaches the sea floor 164, the tip 128a of the spike 110 penetrates and embeds into the sea floor 164. When the spike 110 is embedded into the sea floor 164, a sample of the sea floor 164 is collected into (e.g., fills) the barrel 128c of the spike 110. Water within the barrel 128c can be pushed out of the barrel 128c via holes located at its connection end 128b, such as described elsewhere herein.

After a sample is collected, it is transferred from the barrel 128c of the spike 110 into a sample ampule 108 (e.g., the interior chamber 108c of the ampule 108). In some embodiments, transferring the sample includes actuating the actuation valve 130 located between the spike 110 and the ampule 108. In some embodiments, the actuation valve 130 is actuated by moving from a first position to a second position. For example, the system electronics move the actuation valve 130 from the first position (e.g., a closed position or configuration) to the second position (e.g., an open position). Actuating the actuation valve 130 between the sample spike 110 and the sample ampule 108 renders the barrel 128c of the spike 110 in fluid flow communication with the sample ampule 108 (e.g., the interior chamber 108c).

In some embodiments, a pressure difference between the spike barrel 128c and ampule interior 108c moves the sample from the barrel 128c and into the ampule interior 108c. For example, the ampule 108 is pressurized at the water's surface, and thus has an internal pressure about equal to sea level atmospheric pressure. However, when the device 100 is at the sea floor 164, the pressure outside the ampule 108 (e.g., within the spike barrel) is much greater than sea level atmospheric pressure. When the actuation valve 130 is opened, this pressure difference (e.g., between the spike 110 (sea floor pressure, higher pressure) and the interior 108c of the ampule 108 (surface pressure, lower pressure)) moves (e.g., pushes, pulls, flows) the material contained within the barrel 128c (e.g., the sample of the sea floor) into the ampule interior 108c. In other embodiments, pressure within the ampule 108 can be reduced below sea level atmospheric pressure by removing gases within the ampule 108 (e.g., creation of a vacuum therein), either at the water's surface or during manufacture of the ampule 108. Alternatively, a plunger can be included within the ampule 108, such that drawing back the plunger creates a temporary pressure reduction within the ampule 108, such that the sample is drawn back into the ampule interior 108c from the barrel 128c.

After the sample has been transferred from the spike 110 to the ampule 108, the actuation valve 130 is closed and the attachment subassembly 124 releases the balance weight 118. For example, the system electronics (e.g., the control apparatus) move the actuation valve 130 (e.g., instruct the actuation valve 130 to move) from the second position (e.g., open) to the first position (e.g., closed). The system electronics also actuate the actuators 140, which releases the balance weight 118. Releasing the balance weight 118 reduces the density of the apparatus 100 relative to the water. Accordingly, the device 100 floats to the water's surface (e.g., due to the presence of the float).

When the device 100 reaches the water surface (e.g., floats thereto), it emits a signal that can be detected by a ship (e.g., electronics thereon). The communication subassembly 120 (e.g., the control apparatus, system electronics) is configured to emit at least one of an RF signal, a G.P.S. signal and light (e.g., solid and/or flashing; white and/or colored). In preferred embodiments, the communications subassembly 120 sends an RF signal, a G.P.S. signal and light signals. Additionally, radar detection signals from a search vessel impinge upon the radar angle deflector 160 and are reflected back to the vessel, such that the vessel can locate the device 100 and retrieve it. In some embodiments, a remote communication device (e.g., a computer with a transceiver) can be used to detect and to communicate with (e.g., remotely) the device 100.

After the device 100 has been retrieved, the sampling apparatus 102 is removed. The sample can be removed from the ampule 108, or it can be stored therein. The device 100 can be prepared for re-use by inserting a new (e.g., unused and/or cleaned) sampling apparatus 102 into the ampule housing 112, and attaching a new balance weight 118 onto the attachment subassembly 124. In some embodiments, an electronic device (e.g., a computer) is used to communicate with the system electronics (e.g., control apparatus 106) of the device 100, such as to download (e.g., output) information from the previous dive, to input information related to the next dive, to perform diagnostics and/or reset certain device components (e.g., valves, solenoids, sensors), and the like.

It is to be understood that while certain forms of the present invention have been illustrated and described herein, it is not to be limited to the specific forms or arrangement of parts described and shown.

The invention claimed is:

1. A deep sea floor sampling device for collecting containments when the device sinks to a deep sea floor comprising:

a) a sampling apparatus having a sample ampule with first and second ends and an ampule chamber for receiving the containments from the deep sea floor, a sampling spike with a tip having a barrel opening with an interior surface and connected to the first end of the sample ampule through an actuation valve located between the sampling spike and the sample ampule, the actuation valve having an open position wherein the ampule chamber of the sample ampule is in fluid flow communication with the barrel of the sampling spike and a closed position wherein the fluid flow is blocked between the barrel and the ampule chamber so that the containments of the ampule chamber are sealed in the ampule chamber and not released to and exterior of the ampule chamber when the device rises from the deep sea floor to the top surface of the fluid;

b) a diving apparatus comprising a balance weight operably joined to the sampling apparatus by a selectively activatable release and a float, wherein the balance weight is releasably attached to the sampling apparatus in a manner that the sampling spike extends downwardly a predetermined distance from the bottom surface of the balance weight for penetrating the sampling spike into the deep sea floor to receive the containments including a core sample and a fluid sample from the deep sea floor though the barrel opening of the sampling spike, and wherein the float is attached to the second end of the sample ampule, whereby the device is maintained in a substantially vertical orientation; the balance weight being relative to the sampling apparatus such that an overall density of the device is greater than a fluid the device is to be submerged in when the weight is attached, so that the device sinks and the float being sized relative to the sampling apparatus such that, when the balance weight is released from the diving apparatus after the containments are inserted into the ampule chamber, the density of the device is less than the fluid which the device is submerged in and the float being attached to the sampling apparatus rises to a top surface of the fluid; and wherein the balance weight comprises a metal sinker configured and arranged to sink the device to a depth of at least 5000 feet;

c) a sensor system comprising a sensor for sensing when the device on the sea floor and a drift information sensor for collecting drift information of the device as the device sinks to the deep sea floor and rises to the top surface of the fluid, whereby the position of the sampling device relative to the ambient environment thereof both during descent and ascent between the top surface of the fluid and the deep sea floor is calculable so as to provide a specific location of the sampling device relative to the floor surface when the containments are collected;

d) a control apparatus located within a control housing of the diving apparatus comprising the sensor system and configured to activate the activation valve from the closed position to the open position when the device is on the deep sea floor, to activate the activation valve from the opened position to the closed position after the containments enter the ampule chamber, and to release the balance weight after the valve is in the closed position; and e) a communication subassembly, in communication with the control apparatus and located on top of the float of the diving apparatus, having an antenna for transmitting location information of the device to a remote location when the device is on the top surface of the fluid.

2. The device of claim 1, wherein the float comprises an amount of air sufficient to raise the device from the deep sea floor to the top surface of the fluid.

3. The device of claim 1, wherein the sample ampule is pressurized.

4. The device of claim 1, wherein the communication subassembly comprises one of: an RF antenna, a G.P.S. antenna, and a light.

5. The device of claim 1, wherein the communications assembly comprises a radar reflector.

6. The device of claim 1, the sensor system further comprising a sensor selected from a group consisting of a depth sensor, a pressure sensor, and a temperature sensor.

7. A method of collecting containments of a deep sea floor using a deep sea floor sampling device, comprising:
   a) sinking the deep sea floor sampling device from a surface of a fluid to the deep sea floor; wherein the device comprising a sampling apparatus, a diving apparatus, a sensor system, a control apparatus, and a communication subassembly;
   b) detecting the device being on the deep sea floor by the sensor system of the device; wherein the sensor system comprising a sensor for sensing when the device is on the sea floor and a drift information sensor for collecting drift information of the device as the device sinks to the deep sea floor and rises to the top surface of the fluid, whereby the position of the sampling device relative to the ambient environment thereof both during descent and ascent between the top surface of the fluid and the deep sea floor is calculable so as to provide a specific location of the sampling device relative to the floor surface when the containments are collected
   c) activating an actuation valve which opens a passageway from a sampling spike of the sampling apparatus to a sample ampule by the control apparatus, thereby transferring the containments including a core sample and a fluid sample from a barrel of the sampling spike into the sample ampule of the sampling apparatus;
   d) collecting the containments of the deep sea floor in the barrel of the sampling spike to the sample ampule, having first and second ends and an ampule chamber; wherein the sampling spike with a tip having the barrel opening with an interior surface and connected to the first end of the sample ampule through the actuation valve located between the sampling spike and the sample ampule, the actuation valve having an open position wherein the ampule chamber of the sample ampule is in fluid flow communication with the barrel and a closed position wherein fluid flow is blocked between the barrel and the ampule chamber;
   e) deactivating the actuation valve by the control apparatus after the containments are inserted in the ampule chamber by closing the actuation valve to seal the containments in the sample ampule so as to prevent leakage of the containments from the ampule chamber as the device rises from the deep sea floor to the top surface of the fluid;
   f) returning the device to the fluid top surface by releasing a balance weight of the diving apparatus under a control of the control apparatus after the actuation valve is in the closed position, wherein the diving apparatus comprising the balance weight operably joined to the sampling apparatus by a selectively activatable release and a float, wherein the balance weight is releasably attached to the sampling apparatus and wherein the float is attached to the second end of the sample ampule, whereby the device is maintained in a substantially vertical orientation; the weight being relative to the sampling apparatus such that an overall density of the device is greater than a fluid which the device is to be submerged in when the weight is attached, so that the device sinks to the soil surface and the float being sized relative to the sampling apparatus such that, when the weight is released from the diving apparatus after the containments are inserted into the ampule chamber, the density of the device is less than the fluid which the device is submerged in and the float being attached to the sampling apparatus rises the device to the fluid top surface, wherein the weight is attached to the sampling apparatus in a manner that the sampling spike extends downwardly a predetermined distance from a bottom surface of the weight for penetrating the sampling spike into the sea floor to receive the containments; wherein the balance weight comprises a metal sinker configured and arranged to sink the device to a depth of at least 5000 feet; and
   g) emitting a signal to provide location information of the device when the device is on the fluid top surface using the communication subassembly, in communication with the control apparatus and located on the top of the float of the diving apparatus, having an antenna for transmitting location information of the device to a remote location.

8. The method of claim 7, wherein step of the apparatus returning the sample ampule to the fluid top surface further includes the steps of adjusting the density of the apparatus at the fluid top surface to be greater than that of the fluid and after collecting the sample modifying the density of the apparatus to be less than the density of the fluid.

9. The method of claim 7, further comprising the step of continuously collecting information by the sensor system selected from a group consisting of depth information, temperature information, and pressure information.

10. The method of claim 7, wherein step of the apparatus emitting a signal further comprises the signal being emitted selected from a group consisting of an RF signal, a G.P.S. signal, and light.

* * * * *